US008679426B2

(12) United States Patent
Barrett (10) Patent No.: US 8,679,426 B2
(45) Date of Patent: Mar. 25, 2014

(54) MICROSCOPE ACCESSORY AND MICROPLATE APPARATUS FOR MEASURING PHOSPHORESCENCE AND CELLULAR OXYGEN CONSUMPTION

(75) Inventor: John Barrett, Coral Gables, FL (US)

(73) Assignee: University of Miami, Miami, FL (US)

( * ) Notice: Subject to any disclaimer, the term of this patent is extended or adjusted under 35 U.S.C. 154(b) by 12 days.

(21) Appl. No.: 13/327,188

(22) Filed: Dec. 15, 2011

(65) Prior Publication Data

US 2012/0152403 A1 Jun. 21, 2012

Related U.S. Application Data

(63) Continuation of application No. 13/326,844, filed on Dec. 15, 2011.

(60) Provisional application No. 61/423,670, filed on Dec. 16, 2010, provisional application No. 61/546,692, filed on Oct. 13, 2011.

(51) Int. Cl.
*B01L 3/00* (2006.01)

(52) U.S. Cl.
USPC .............................. 422/552; 422/553; 422/550

(58) Field of Classification Search
USPC .......................................... 422/552, 553, 550
See application file for complete search history.

(56) References Cited

U.S. PATENT DOCUMENTS 6,485,690 B1 * 11/2002 Pfost et al. ..................... 422/552

OTHER PUBLICATIONS

Martin D. Brand et al., "Assessing mitochondrial dysfunction in cells", Biochem. J, (2011), 435, 297-312, Great Britain.

D. Renker, "Geiger-mode avalanche photodiodes, history, properties and problems", Nuclear Instruments and Methods in Physics Research A, 567, (2006), 48-56.

Naser Faramarzpour et al., "Fully Integrated Single Photon Avalance Diode Detector in Standard CMOS 0.18-μm Technology", IEEE Transactions on Electron Devices, Mar. 2008, vol. 55, No. 3, 760-767.

N. S. Nightingale, "A New Silicon Avalanche Photodiode Photon Counting Detector Module for Astronomy", Experimental Astronomy 1, (1991), 407-422, Netherlands.

Andreas Fercher et al., "Evaluation of the derivates of phosphorescent Pt-coproporphyrin as intracellular oxygen-sensitive probes", Anal Bioanal Chem, (2010), 396: 1793-1803.

Akos A. Gerencser et al., "Quantitative Microplate-Based Respirometry with Correction for Oxygen Diffusion", Analytical Chemistry, vol. 81, No. 16, Aug. 15, 2009, 6868-6878.

Aleksander S. Golub et al., "Phosphorescence quenching microrespirometry of skeletal muscle in situ", Am J Physiol Heart Circ Physiol, (2011) 300: H135-H143.

(Continued)

*Primary Examiner* — Natalia Levkovich
(74) *Attorney, Agent, or Firm* — Christopher & Weisberg, P.A.

(57) ABSTRACT

A microplate apparatus having a bottom plate defining a plurality of very small microwells (for example, each having a volume of 0.02 or less) for containing sample material and a top plate defining a plurality of domes, each of which housing a sensors for measuring biological parameters, such as cellular oxygen consumption, pH changes, calcium uptake, and metabolic reduction of fluorescent dyes. The top and bottom plates may be composed of quartz. The microplate assembly may be fabricated using a method involving applying an etching solution to each of the top and bottom plates to create the domes and microwells. Additionally, etching solution may be applied to the bottom plate to create a raised lip region around each of the microwells. The etched-away areas surrounding the lip regions facilitate the changing of microwell solution without disrupting the samples.

9 Claims, 9 Drawing Sheets

(56) References Cited

OTHER PUBLICATIONS

Nicolas Maindron et al., "Synthesis and luminescence properties of new red-shifted absorption lanthanide (III) chelates suitable for peptide and protein labelling", Organic & Biomolecular Chemistry, 2011, 9:2357-2370.

Timothy W. Molter et al., "A New Approach for Measuring Single-Cell Oxygen Consumption Rates", IEEE Trans Autom Sci Eng., Jan. 1, 2008; 5(1): 32-42.

Timothy W. Molter et al., "A microwell array device capable of measuring single-cell oxygen consumption rates", Sens Actuators B Chem. Jan. 15, 2009; 135(2): 678-686.

Doris Nonner et al., "Bone morphogenetic proteins and neurotrophins provide complementary protection of septal cholinergic function during phosphate inhibitor-induced stress", Journal of Neurochemistry, (2004), 91: 77-87.

Jaehyun Park et al., "A microsystem for sensing and patterning oxidative microgradients during cell culture", Lab Chip, 2006, 6: 611-622.

Ryan A. Colyer et al., "High-throughput FCS using an LCOS spatial light modulator and an 8×1 SPAD array", Biomedical Optics Express 1408, Dec. 1, 2010, vol. 1, No. 5, 1408-1431.

Elly Sinkala et al., "Oxygen sensitive microwells", Lab Chip, 2010, 10, 3291-3295.

Mario Stipcevic "Active quenching circuit for single-photon detection with Geiger mode avalanche photodiodes", Applied Optics, Mar. 20, 2009, vol. 48, No. 9, 1705-1714.

Mario Stipcevic et al., "Characterization of a novel avalanche photodiode for single photon detection in VIS-NIR range", Optics Express, Aug. 2, 2010, vol. 18, No. 16, 17448-17459.

Timothy J. Strovas et al., "Direct measurement of oxygen consumption rates from attached and unattached cells in a reversibly sealed, diffusionally isolated sample chamber", Adv Biosci Biotechnol. Dec. 1, 2010; 5(5): 398-408.

Yanqing Tian et al., "A New Crosslinkable Oxygen Sensor Covalently Bonded into Poly (2-hydroxyethyl methacrylate)-CO-Polyacrylamide Thin Film for Dissolved Oxygen Sensing", Chem Mater, Mar. 23, 2010; 22(6): 2069-2078.

Peter C. Thomas et al., "A noninvasive Thin Film Sensor for Monitoring Oxygen Tension during in Vitro Cell Culture", Analytical Chemistry, vol. 81, No. 22, Nov. 15, 2009, 9239-9246.

Vijay S. Tripathi et al., "Optical oxygen sensors based on platinum porphyrin dyes encapsulated in ORMOSILS", Sensors and Actuators, B 147, (2010), 741-747.

\* cited by examiner

MICROSCOPE ACCESSORY AND MICROPLATE APPARATUS FOR MEASURING PHOSPHORESCENCE AND CELLULAR OXYGEN CONSUMPTION

CROSS-REFERENCE TO RELATED APPLICATION

This application is related to and claims priority to U.S. Provisional Patent Application Ser. No. 61/423,670, filed Dec. 16, 2010, entitled PLATEREADER DEVICE FOR MEASURING SINGLE CELL OXYGEN CONSUMPTION, and U.S. Provisional Patent Application Ser. No. 61/546,692, filed Oct. 13, 2011, entitled MICROSCOPE ACCESSORY FOR WHOLE WELL FLUORESCENCE AND TIME RESOLVED PHOSPHORESCENCE MEASUREMENTS, the entirety of both of which are incorporated herein by reference.

STATEMENT REGARDING FEDERALLY SPONSORED RESEARCH OR DEVELOPMENT n/a

FIELD OF THE INVENTION

The present invention relates to the field of microscopy and, in particular, to adapting a traditional microscope system to read fluorescence/phosphorescence signals with high accuracy. It also relates to the field of using phosphorescent sensors to measure cellular oxygen consumption and to platereader technology with small microwells.

BACKGROUND OF THE INVENTION

Fluorescence and time-resolved phosphorescence plate readers are commonly used in time-resolved spectroscopy when evaluating dynamic processes in organisms, materials, or chemical compounds by means of spectroscopic techniques. Plate readers detect biological, chemical, or physical changes in samples contained within microtiter plates, and the measurements are usually based on the optical phenomena of absorbance, fluorescence intensity, luminescence, time-resolved fluorescence, and fluorescent polarization.

Although plate reader systems, such as those used with enzyme-linked immunosorbent assay (ELISA) reader, may efficiently and accurately measure biological parameters of a sample, they have associated disadvantages. Also, most platereaders do not work well with very small wells, for example, of less than 500-micron diameter. For example, diseases and conditions related to mitochondria dysfunction, such as muscle weakness, exercise intolerance, and amytrophic lateral sclerosis, may become detectable by measuring in a sample the rate of cellular oxygen consumption. However, the larger well sizes of standard microtitre plates (which are often as large as 100 to 200 microliters) fail to provide the necessary sensitivity to measure single-cell oxygen consumption. Finally, typical methods for measuring oxygen consumption with very small samples use charge coupled device (CCD) cameras for detecting phosphorescence, which can contribute significantly to the cost of the system. Not only are CCD cameras costly, but they can also be bulky and have a limited effective dynamic range (typically 8-10 bits).

The inverted microscope is relatively inexpensive and is a staple piece of laboratory equipment for observing living cells or organisms more easily than on a glass slide (as is used with a conventional microscope). However, an inverted microscope is not capable of taking the biological activity measurements of a plate reader, such as time-resolved phosphorescence measurements or very high accuracy quantitation of fluorescence changes with time. Both low cost, biological assessment capabilities, and traditional imaging is therefore desired.

Another medical tool for imaging and measuring biological parameters is fluorescence bronchoscopy. This technique is based on the principal that normal tissue fluoresces differently than diseased tissue when exposed to certain wavelengths of light. Many bronchoscopes use an ordered fiber optic array to detect this fluorescence and locate areas of damaged tissue. One problem with relying on fluorescence, however, is that body tissue may contribute a significant amount of background fluorescence noise. Therefore, an alternative and more accurate method of imaging diseased tissue is desired.

Provided herein is a device and system that not only expands the capabilities of a traditional inverted microscope by adding time-resolved plate-reader functionality, but also improves accuracy of the measurement of sample phosphorescence, including biological tissue in vivo. The device, which may be sized to fit into the condenser holder of an inverted microscope, provides plate-reading function at very low cost compared to that of traditional plate reader units, and also allows for the correlation of plate reader measurements with actual images of a specimen. Additionally, the device provides a much higher x-y spatial resolution than typical plate readers, and so allows for more accurate measurements from very small microwells, even as small as 100 microns in diameter or less. This feature is useful in high throughput screening, and the very small wells also enable more accurate measurements of cellular oxygen consumption even at the single cell level. Finally, the device and system also are able to measure other parameters associated with cell metabolism, such as pH changes, calcium uptake, and metabolic reduction of fluorescent dyes such as resorufin, in addition to and oxygen levels.

SUMMARY OF THE INVENTION

The present invention advantageously provides a system and device that allows an inverted microscope with a movable x-y stage to also function as a time-resolved plate reader, for example, to measure and image phosphorescence. The present invention also advantageously provides a microplate apparatus comprising a quartz lid plate having a plurality of domes, a quartz bottom plate having a plurality of microwells, each microwell corresponding to a dome, one or more sensors located in each dome, a compressible gasket located between the lid plate and bottom plate, and an inlet tube and an outlet tube each being in fluid communication with the plurality of microwells. The microplate apparatus may further include a plurality of lip regions, each of which substantially circumscribing each microwell. The microplate apparatus may further include an internal space between the lid plate and bottom plate that is configured to contain a volume of solution and is in fluid communication with the input tube and the outlet tube. Further, a pressure may be exerted on the lid plate and the bottom plate to at least partially compress the compressible gasket. The microplate apparatus may further include a stop element that prevents the lid plate from rising above the microplate at a distance greater than approximately 500 microns. The one or more sensors of the microplate apparatus may include at least one of: pH sensor, oxygen sensor, fluorescent/phosphorescent probe, phosphorescent fluorescent temperature sensor, nitric oxide sensor, and standard fluorescent probe. The one or more sensors may be Pt-porphyrin probes, and the Pt-porphyrin probes may be embedded within a film of oxygen-permeable silicone. Further, the bottom of each of the plurality of microwells of the microplate assembly may be coated with a layer of poly-L-lysine. Further, each microwell may have a volume of approximately 0.2 µL or less.

The present invention also advantageously provides a method of making a microplate apparatus, comprising: providing a first quartz plate and a second quartz plate, providing a mask for each of the first and second quartz plates, the masks having a plurality of voids and covering at least a portion of each of the first and second quartz plates, putting the masks in contact with each of the first and second quartz plates, and applying an etching solution to the unmasked portions of each of the first and second quartz plates, the etching solution creating a plurality of wells in the first and second quartz plates corresponding to each of the plurality of voids in the mask. The method may further include: providing a first block to which the first mask is adhered, and a second block to which the second mask is adhered, each of the first and second blocks having a fluid path, clamping the first and second quartz plates between the first and second blocks, and applying the etching solution to the first and second quartz plates through the fluid path of each block. Further, each of the plurality of wells may have a diameter of less than approximately 400 µm. Further, the mask is composed of Teflon or polypropylene. Further, the etching solution comprises 6% hydrofluoric acid and 5% hexafluoric acid.

The present invention also advantageously provides a method for changing a solution within a microplate apparatus comprising: providing a microplate including a lid plate having a plurality of domes, a bottom plate having a plurality of microwells, each microwell corresponding to a dome, one or more sensors located in each dome, a compressible gasket located between the lid plate and bottom, one or more spaces defined by the lid plate, bottom plate, and compressible gasket configured to contain a volume of solution, a stop element, an inlet tube in fluid communication with the one or more spaces, and an outlet tube in fluid communication with the one or more spaces, wherein a pressure is exerted on the lid plate and bottom plate to at least partially compress the compressible gasket; releasing the pressure exerted on the lid plate and bottom plate, the compressible gasket remaining in contact with the lid plate and bottom plate, plugging the outlet tube so that fluid cannot exit the microplate apparatus, injecting a volume of solution through the inlet tube into the one or more spaces, unplugging the outlet tube, and reapplying the pressure exerted on the lid plate and bottom plate to expel excess solution not contained within the plurality of microwells from the one or more spaces through the outlet tube. Further, the stop element may be positioned to stop the lid plate from rising more than approximately 500 µm when the volume of solution is injected through the inlet tube. Further, each microwell is sized to contain a volume of approximately 0.2 µL. Further, the lid plate and bottom plate may be composed of quartz. Further, the pressure is generated by a clamp apparatus comprising: a frame at least partially in contact with the lid plate, a plurality of compression springs coupled to the frame, a plurality of solenoids coupled to the frame, a plurality of release levers coupled to the frame, each release lever having a first end and a second end, each first end in contact with a solenoid and each second end in contact with a compression spring, a plurality of fulcrums, each fulcrum being a pivot point for a release lever, and a power source in electrical communication with the plurality of solenoids. Further, an electrical charge from the power source may be applied to the plurality of solenoids when adding a solution, and the electrical charge from the power source may be discontinued to exert pressure from the frame of the clamp apparatus on the lid plate.

BRIEF DESCRIPTION OF THE DRAWINGS

A more complete understanding of the present invention, and the attendant advantages and features thereof, will be more readily understood by reference to the following detailed description when considered in conjunction with the accompanying drawings (which may not be drawn to scale) wherein.

DETAILED DESCRIPTION OF THE INVENTION

Figure 1A:
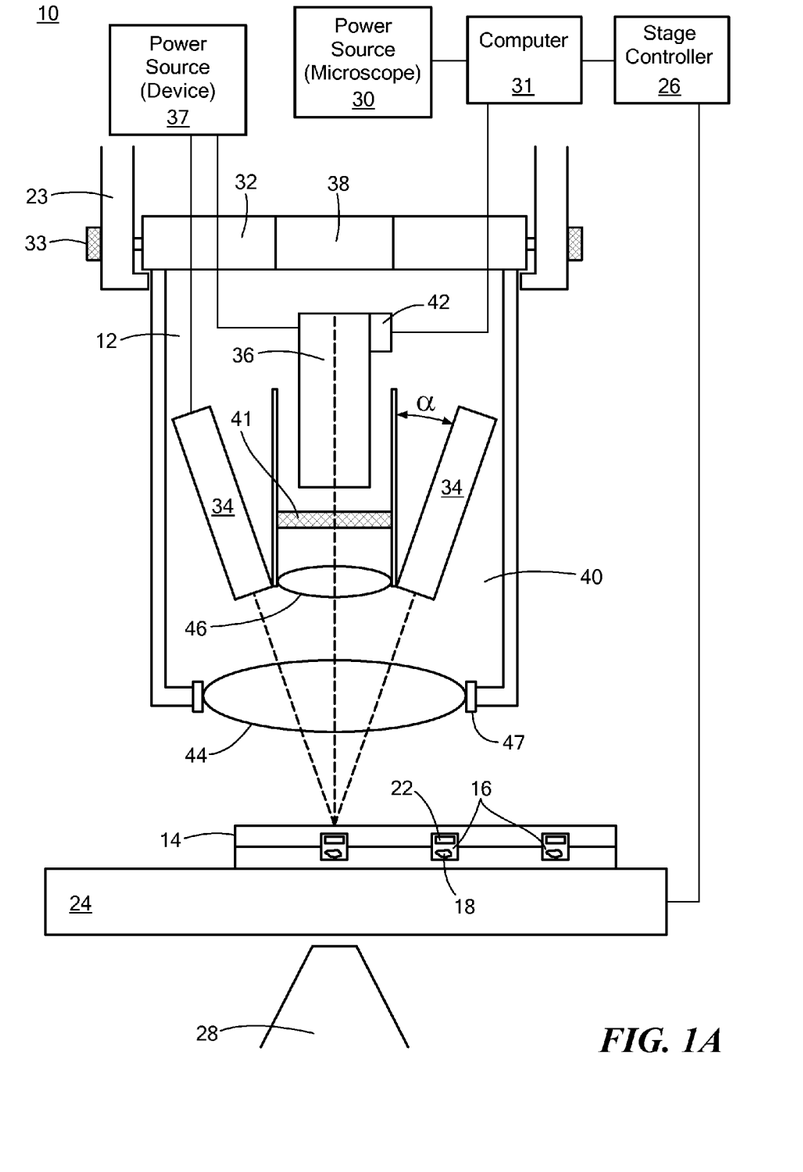
FIGS. 1A and 1B show schematic representations of a first embodiment of a device and system in accordance with the principles of the present invention.
Figure 1B:
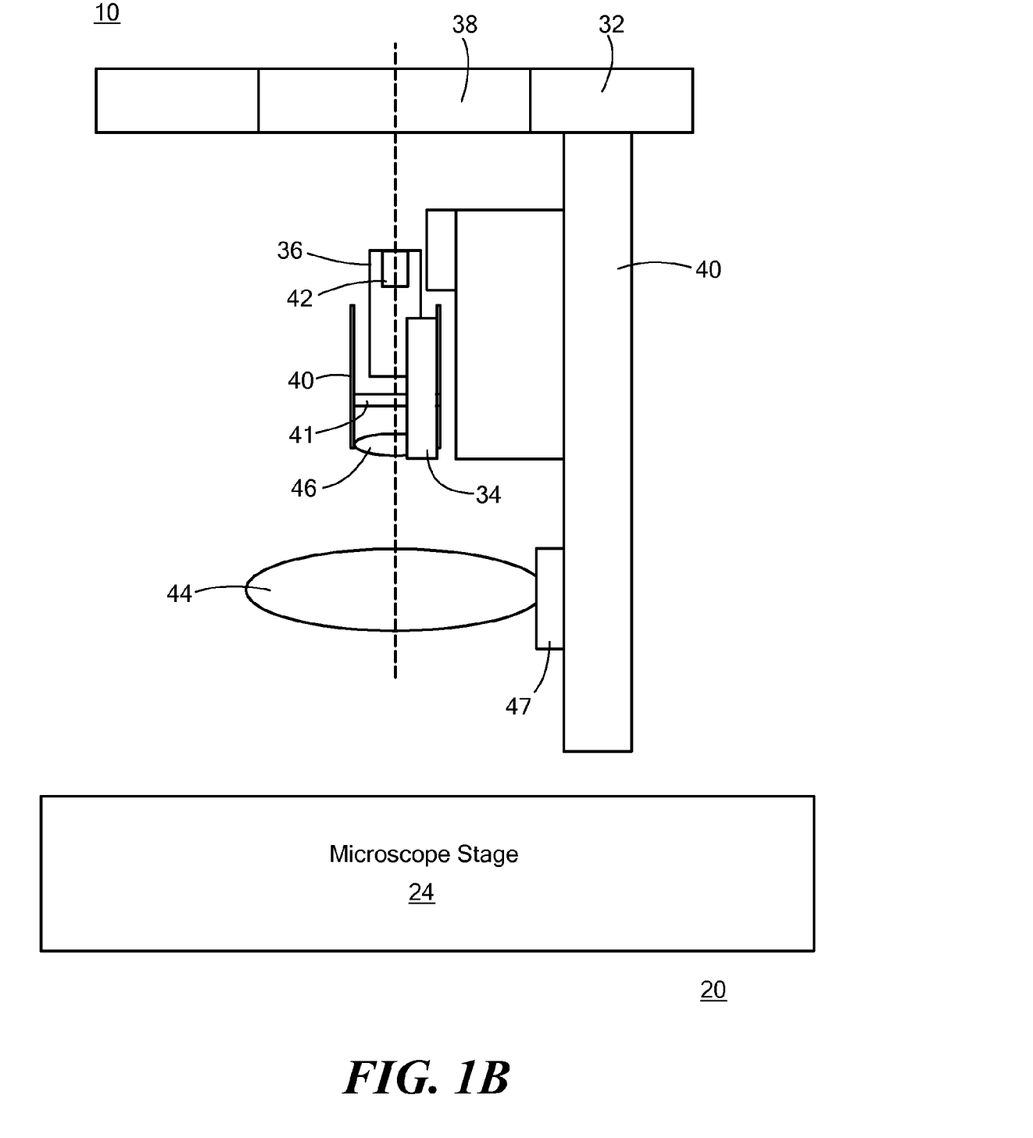

Referring now to FIG. 1A (front view) and 1B (side view), schematic representations of a first embodiment of a system 10 and device 12 in accordance with the principles of the present invention are shown. The system 10 may generally include a phosphorescence measurement device 12, a sample holder 14 having a plurality of sample wells (or "microwells") 16 in which one or more samples 18 may be contained, and an inverted microscope 20 for imaging the samples 18. The sample holder 14 may further include one or more sensors 22 for measuring oxygen levels, changes in pH, or other parameters.

The inverted microscope 20 may further include a condenser holder 23, a movable (for example, motorized) x-y and/or x-y-z stage 24 at a predetermined or variable distance from the condenser holder and in electrical communication with a stage controller 26. The inverted microscope 20 may further include one or more microscope objective lenses 28 for imaging the samples 18. Additionally, the inverted microscope 20, system 10, and device 12 may be connected to a power source 30, a computer 31, and one or more monitors, displays, and/or user input devices (not shown) used to display generated images, to control system parameters, and to operate the stage 24 of the microscope 20.

The sample holder 14 (such as a microplate assembly) may be positioned on the stage 24, from which the system 10 may image the samples 18 and detect phosphorescence emitted from the samples 18. That is, the system may perform both traditional microscopy and plate reader functions. Additionally, the motorized stage 24 may allow for the precise movement from one microwell 16 to the next when either imaging or measuring phosphorescence (light emitted with a delay following excitation) emitted from the samples 18.

The one or more sensors 22 may be $O_2$-sensitive probes, such as platinum (Pt) porphyrin, that emit phosphorescence perceivable by the device 12. Pt-porphyrin has excitation peaks at approximately 370 nm and approximately 530 nm (which may be used for measuring oxygen consumption in the sample 18), and has an emission wavelength of approximately 650 nm. Excitation light pulses (for example, approximately 370 nm or approximately 530 nm) emitted from the one or more light sources 34 may excite the Pt-porphyrin oxygen-sensitive sensor, that is, drive Pt-porphyrin electrons to a higher energy level, creating excited-state Pt-porphyrin molecules. Collisions between the excited-state Pt-porphyrin molecules and $O_2$ molecules may quench the excited-state Pt-porphyrin molecules (that is, cause the Pt-porphyrin molecules to lose the excited state). The higher the $O_2$ concentration within the sample 18, the more rapid the decay of the excited-state Pt-porphyrin molecules (quenching).

Additionally or alternatively, other sensors 22 may be used to measure biological data from a sample 18, for example, pH sensors, different oxygen sensors, fluorescent/phosphorescent probes, phosphorescent fluorescent temperature sensors, nitric oxide sensors, and standard fluorescent probes. A pH sensor may include dyes whose fluorescence is pH sensitive such as fluorescein, BCECF, and SNARF dyes. Other probes or dyes could also include phosphorescent probes for immunochemistry (for example, Europium-, Turbium-, or porphyrin-labeled antibodies) and fluorescent probes used to measure aspects of cellular function such as rhodamine 123, JC1, and TMRM for mitochondrial potential, and many fluorescent ion sensitive dyes (for example, Fura or Oregon Green BAPTA series for $Ca^{+2}$ from Molecular Probes, Inc.). Recombinant fluorescent proteins that are sensitive to cellular ions (for example, YFP for pH changes) may also be useful. If fluorescent labels are used, microscopy can also be used to image and identify sample fluorescence. Most fluorescent labels do not interfere with the oxygen-sensitive phosphorescence measurements because fluorescence emissions may occur only during the excitation of light and the first approximately 10-20 nanoseconds following excitation, whereas relevant phosphorescence measurements (such as by using Pt-porphyrin) may occur over longer post-excitation intervals (for example, 10 to 500 microseconds). Additionally, the excitation and emission wavelengths may not interfere substantially with the wavelengths used by many fluorescent labels.

The device 12 may have a proximal end 12a that may include a microscope mounting bracket 32 for affixing the device 12 to the condenser holder 23 of the inverted microscope 20, and a distal end 12b that may be directed toward the samples 18. The device 12 may be aligned and secured within the condenser holder 23 by tightening condenser holder screws 33 against the mounting bracket 32. The device 12 may further generally include one or more light sources 34 to apply an excitation light flash to a sample 18, and a sensitive light detector 36 to measure sample phosphorescence. The device 12 shown in FIG. 1 may be sized and configured to be installed within the condenser holder 23 of any traditional inverted microscope 20, such that the device 12 fits between the condenser holder 23 and the sample holder 14, the device 12 not being in contact with the sample holder 14. Further, the device 12 may be in electrical communication with the microscope 20 and/or an external power source 37 and/or computer 31. The mounting bracket 32 may have substantially horizontal alignment relative to the base of the microscope 20 (that is, substantially parallel to the stage 24), but may be any of a variety of shapes, dimensions, and orientations, depending on the shape and style of the condenser holder 23. Further, the mounting bracket 32 may include an aperture 38 that allows light to pass therethrough.

The device 12 may further include a frame 40, having a substantially vertical alignment, connected to the mounting bracket 32. The frame may at least partially enclose the device 12 and may function as a light shield (blocking atmospheric and "noise" light from entering the device). The frame 40 may be composed of materials such as plastic, acrylic, or metal. Further, the frame 40 may be any of a variety of sizes or configurations, as long as the frame 40 does not prevent the device 12 from being mounted to the inverted microscope 20 between the condenser holder 23 and the sample holder 14, the device 12 not being in contact with the sample holder 14. The various elements of the device 12 may be affixed to the frame 40, as detailed below.

The one or more light sources 34 may be light-emitting diodes (LEDs) or laser diodes that emit, for example, excitation pulses at 370-nm wavelengths or 532 nm wavelengths. Depending on the type of light source used, the one or more light sources 34 may each be positioned to direct light at a common convergence point. Therefore, if, for example, two light sources 34 are used, the light sources 34 may be affixed to the frame 40 at an angle to the vertical (y) axis (for example, 15 degrees), represented in FIG. 1A as a. The direction of the light emitted from the one or more light sources 34 may be more precisely determined if, for example, laser diodes are used than if LEDs are used. The one or more light sources 34 may each include one or more lenses (not shown), and/or one or more lenses may be positioned within the light path, for directing the excitation light. An emission filter 41, also affixed to the frame 40, may be included prevent reflected excitation light from interfering with the detection of phosphorescence. Because the phosphorescence emitted by the samples 18 may spread in a direction largely independent of the angle of excitation light, the design of the device does not reduce detection efficiency for the emitted light. General directions of light are represented in FIGS. 1A and 1B using dashed lines. Although the directions are shown as single lines, it will be appreciated that a light source such as an LED may send light beams in multiple directions, whereas light from a source such as a laser diode will be directed in a substantially singular linear direction.

The sensitive light detector (SLD) 36 may be an avalanche photodiode (APD) or, alternatively, a small photomultiplier tube used in photon-counting mode or linear mode with a counter-timer peripheral component interconnect (PCI) board 42, such as the Omega Inc. PLI DACboard 3006 or PCI-1780 from Advantech (which have multiple counters and multiple timers), which is in electrical communication with a computer or other data processing device 31. The PCI board 42 may control both the light source 34 excitation pulses and the counting of detected photons during specified intervals following each excitation pulse. Because APDs have a smaller size, a greater effective dynamic range, and greater sensitivity than gated, image-intensified CCD cameras typically used in plate reader devices, APDs are well-suited for measuring the full time course of $O_2$-sensitive decay of phosphorescence emitted by the samples 18. To reduce noise, the SLD 36 may be at least partially enclosed within the frame 40. Further, the system 10 may be programmed to count APD circuit output pulses over multiple intervals simultaneously, whereas a CCD camera counts during only one interval at a time. The output of the PCI board 42 may be uploaded to the computer 31 through a PCI or USB interface (not shown), depending on the type of PCI board 42 used in the device 12.

The device 12 may further include one or more lenses, such as a main lens 44 and relay lens 46 used for directing and focusing the light from the one or more light sources 34 to the samples 18 (main lens 46) and from the samples 18 and/or sensors 22 back into the SLD 36. The lenses 44, 46 may be simple lenses of any configuration. Additionally, although it may not be depicted as such in the figures, each lens 44, 46 may be a collection of simple lenses sharing a common axis (compound lens or doublet lens), as these may correct for spherical and chromatic aberrations. Further, the main lens 44 may be a microscope objective lens (for example, a 20× objective) that is coupled to the frame 40. Further, the main lens 44 may be interchangeable (for example, a 20× objective may be replaced with a 10× objective). The main lens 44 and relay lens 46, whether being a simple or compound lens, may each have a lens axis, a focal point (the point at which the lens, whether simple or compound, focuses on an object) and image plane (the plane at which the lens, whether being a simple or compound lens, focuses on an object). The lenses 44, 46 may be affixed to the frame 40 using a lens mounting bracket 47, such as a screw-type bracket into which the main lens 44 may be mounted. The lenses 44, 46 may be positioned distal to the SLD 36 and emission filter 41 and may be substantially perpendicular to the angle of light reflected from the sample 18 into the SLD 36. The lenses 44, 46, emission filter 41, and SLD 36 may be aligned or substantially aligned along a substantially vertical axis, which may also be the lens axis. The substantially vertical axis may be substantially perpendicular to the plane of the surface of the microscope stage 24. Further, the lenses 44, 46 may be movable in relation to the stage 24, or the stage 24 may be movable in relation to the lenses 44, 46.

Further, the lenses 44, 46 may be operable in two modes. In the first mode, light reflected from the sensors 22 may be focused entirely within the sensitive region of the SLD 36 for measuring the phosphorescence from the sensors 22. In the second mode, only a portion of the samples 18 may be focused on the sensitive region of the SLD 36 so as to enable the system 10 to generate high resolution images in the scanning (imaging) mode.

The device 12 may further include an analog-to-digital converter 49 (such as a 16-bit converter) for converting the SLD 36 data to a digital representation. The SLD 36 may put out a voltage/current signal in response to light, which the analog-to-digital converter 49 may sample and send the data to the computer 31.

Figure 2:
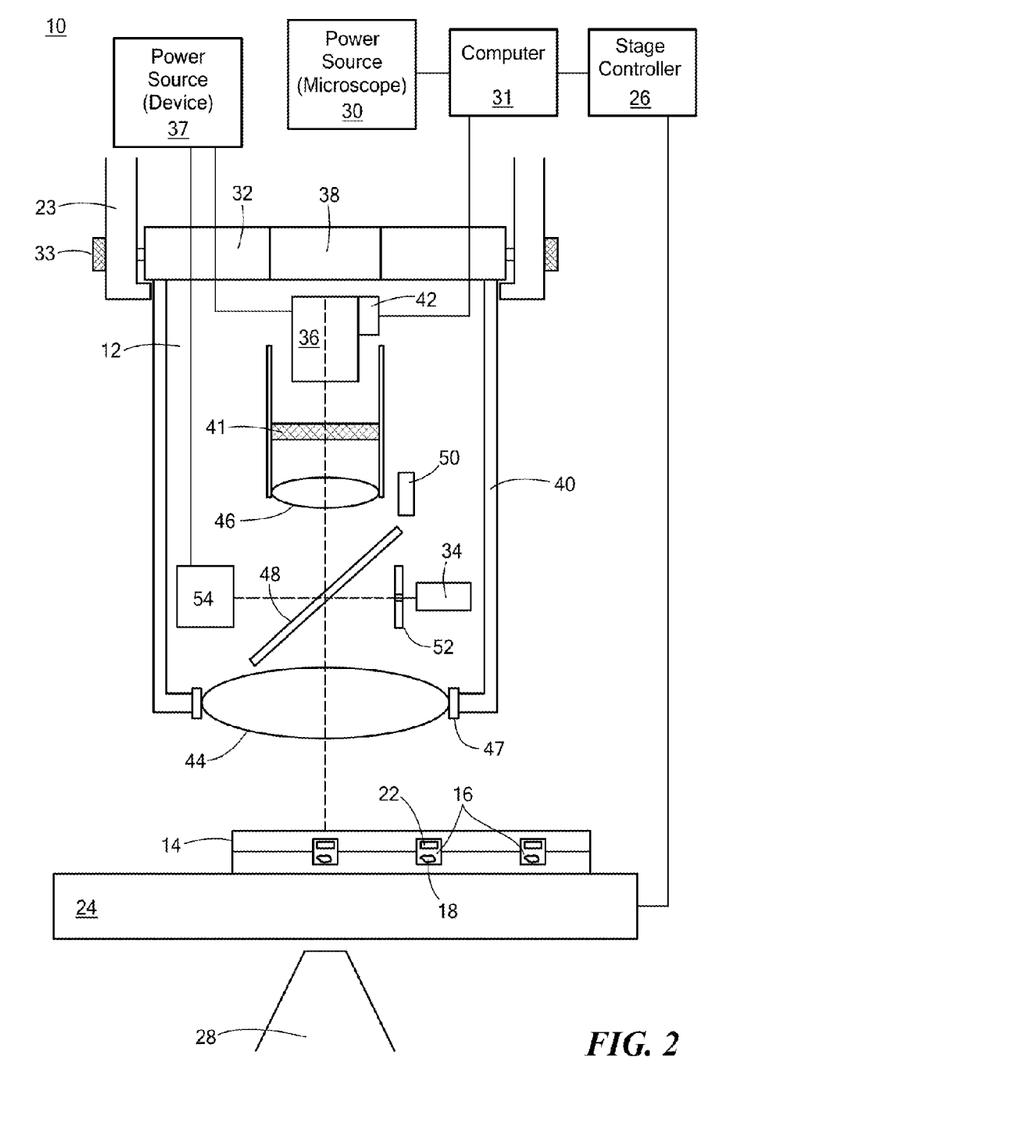
FIG. 2 shows a schematic representation of a second embodiment of a device that is sized to fit into the condenser holder of an inverted microscope in accordance with the principles of the present invention.

Referring now to FIG. 2, the device 12 may further include an optical device 48 that may direct at least a portion of the light from the one or more light sources 34 to the microwells 16 and at least a portion of the light to the SLD 36. The optical device 48 may be, for example, a dichroic filter or beam splitter that has long pass wavelength characteristics, that is, it allows light with wavelengths of greater than 550 nm emitted by the sample 18 to pass through to the SLD 36. Although the first embodiment of the device 12 as shown in FIGS. 1A and 1B may be more compact and less expensive than the embodiment including an optical device 48 such as a dichroic filter, it may not produce the same image quality. Thus, the first embodiment may be suitable when low cost and simplicity of design is more important than high-resolution imaging, or when only phosphorescence measurements are to be taken. On the other hand, if image quality if of significant importance, the second embodiment as shown in FIG. 2 may be used.

Continuing to refer to FIG. 2, the device 12 may further include one or more light shields 50 to minimize interference by light "noise" (light not emitted from the one or more light sources 34 or reflected from the microwells 16), and one or more iris diaphragms 52 to control the amount of light that passes from the one or more light sources 34 to the optical device 48. However, the frame 40 itself may function as a light shield. The intensity of the light excitation pulses may be monitored by a fast photodiode 54 (such as ThorLabs FDS 100) positioned behind the optical device 48. The optical device 48 may be located so as to direct light emitted by the samples 18 in the vertical direction and into the SLD 36, and may also be located on a direct horizontal line passing from the one or more light sources 34 to the fast photodiode 54, thus able to direct at least a portion of the light form the one or more light sources 34 to the fast photodiode 54. The one or more light sources 34, optical device 48, fast photodiode 54, one or more light shields 50, and one or more iris diaphragms 52 may all be affixed to the frame 40. General directions of light in FIG. 2 are represented using dashed lines.

Figure 3:
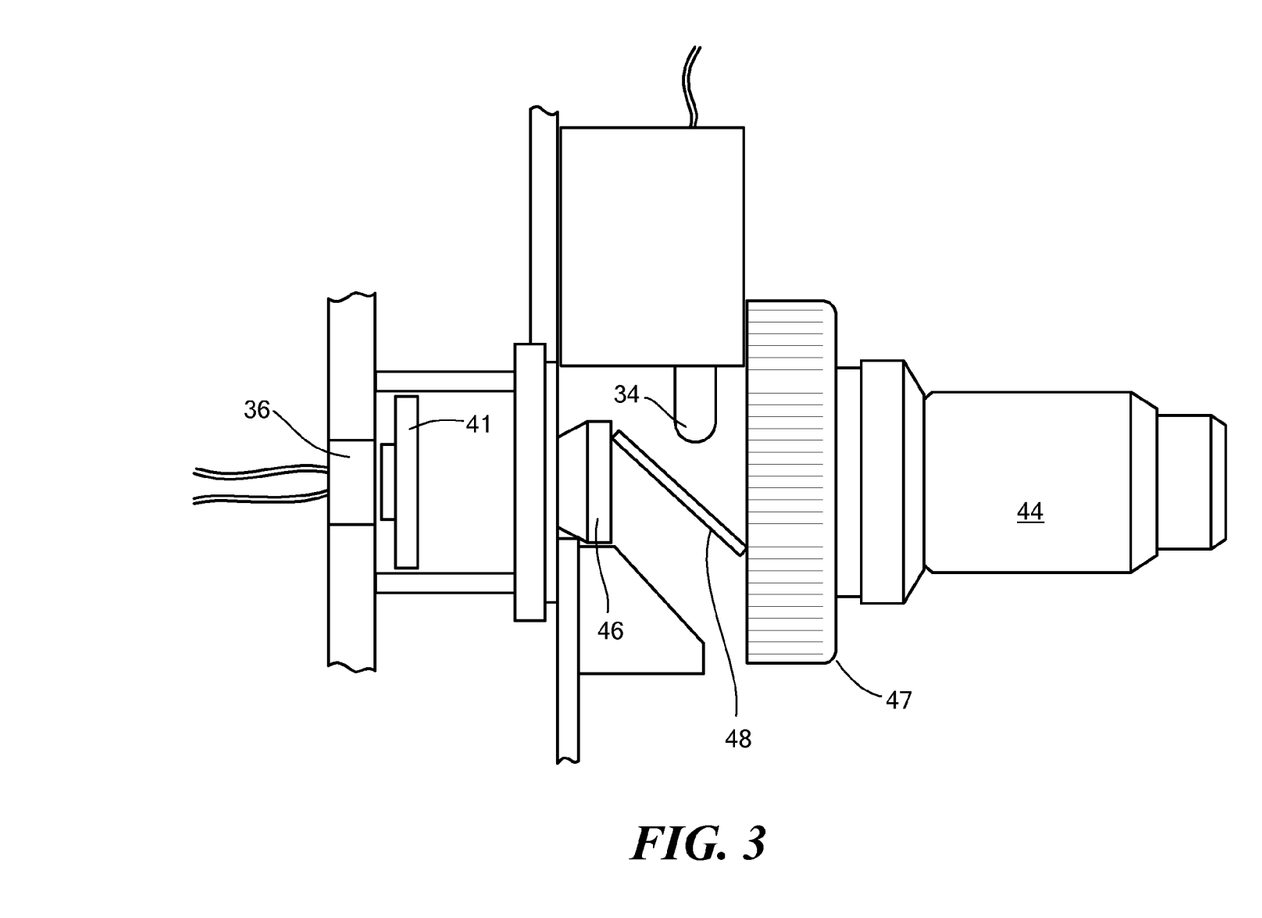
FIG. 3 shows a second embodiment of a device that is sized to fit into the condenser holder of an inverted microscope in accordance with the principles of the present invention.

Referring now to FIG. 3, a second embodiment of a device that is sized to fit into the condenser holder is shown. The device 12 shown in FIG. 3 may be representative of the configuration of a device 12 according to FIG. 2 (second embodiment). For example, the device 12 shown in FIG. 3 may include a mounting bracket 23, an avalanche photodiode 36, an emission filter 41, a relay lens 46, a light source 34, an optical device 48, a fast photodiode 54, a lens mounting bracket 47, and a main lens 44. The device 12 may further include other elements shown and described in FIG. 2.

As an example of the phosphorescence-measuring functionality of the system 10 as shown in any of FIGS. 1A, 1B, and 2, a phosphorescence measurement cycle begins with a short (1 to 10 μsec) excitation light pulse from the one or more light sources 34 directed toward the samples 18 within the sample holder 14. The light may be sent directly to the samples 18 either through one or more lenses 44, 46 (as in FIGS. 1A and 1B) or through the optical device 48 (as in FIG. 2). In this particular example, the sensors 22 may be Pt-porphyrin sensors for measuring oxygen consumption in the samples 18. Phosphorescence from the sample 18 within the sample holder 14 may be projected to the SLD 36 by a short focal length relay lens 46 that may focus the light within the SLD 36. The SLD 36 may be connected to a Geiger mode circuit that outputs a 5V transistor-transistor logic (TTL) pulses for each photon detected by the SLD 36 during specified intervals during and following the light excitation light pulse. For example, three intervals may be used: 0-5 μsec, 20-120 μsec, and 120-320 μsec intervals. These pulses may then be counted by the PCI board 42. Each light pulse and measurement cycle may be repeated 100 to 500 times at 1 kHz, and the computer 31 may calculate the average number of photons detected in each time interval.

The system 12 may also be used to generate images of the samples 18, including images of the phosphorescence in the microwells 16. Phosphorescence imaging may have an application in immunohistochemical studies, such as screening for cancer antigens. Such spatial measurements may be obtained by including a pulsed laser diode as the one or more light sources 34, and altering the distance and relay lens 46 focal length to project a larger image of the samples 18 onto the SLD 36. In this imaging mode, the x-y raster scanning motion of the motorized microscope stage 24 may be used to sample phosphorescence at different locations. A constant velocity raster mode of the motorized microscope stage 24 may output a TTL pulse from the stage controller 26 at the beginning of each line scan. Using these pulses and the known velocity of the stage 24, a computer program may calculate the position at which each phosphorescence measurement was taken, and use this information to generate an image of the phosphorescence that should be spatially accurate to within 1 μm. Computer control of the z-axis of the microscope focusing system may allow for scanning at different depths within a sample 18.

In addition to imaging phosphorescence in sample holder 14 samples 18, such imaging may be performed in vivo using the system 10 and device 12 in association with an ordered fiber optic array. Ordered fiber optic arrays are used in the medical field, for example, in bronchoscopy. In an alternative embodiment not shown, the device 12 may be in electrical communication with an external power source 37, an inverted microscope 20, a computer 31, and one or more monitors, displays, and/or user input devices. An ordered fiber optic array may be connected to the device 12, and may have a proximal end in optical communication with the device 12, and a distal end that may be placed in contact with body tissue. Further, a different x-y controller, such as a piezoelectric x-y controller, may replace the microscope and x-y stage 24, to move the proximal end of the fiber optic array in relation to the device 12. This configuration may allow quantification of cancer antigens within the human body using phosphorescence instead of fluorescence, as is presently used in techniques such as bronchoscopy.

Figure 4:
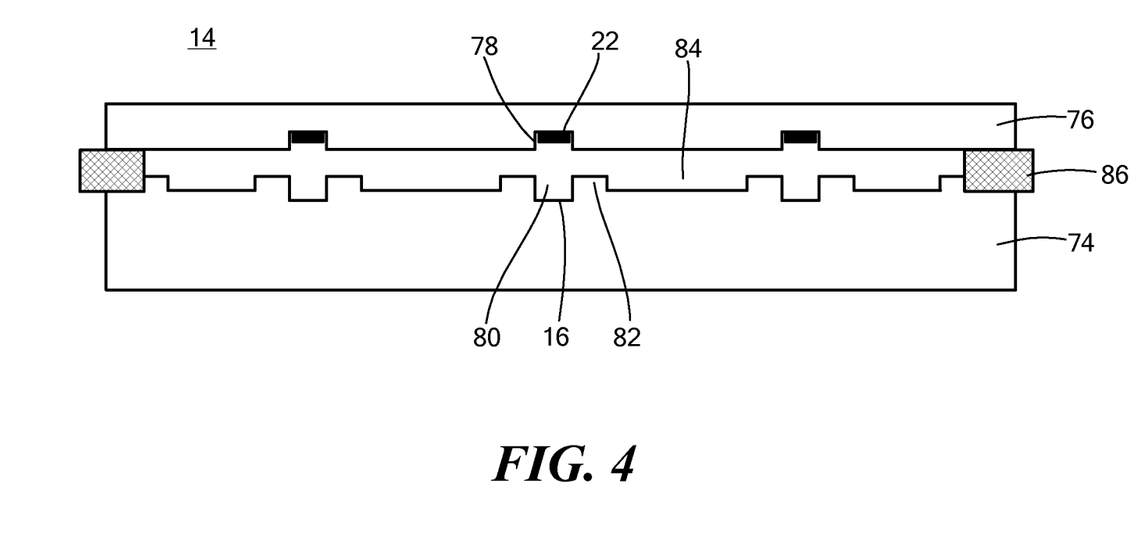
FIG. 4 shows a cross-section view of an embodiment of a microplate apparatus including a Pt-porphyrin sensor embedded in a silicone resin being located within each dome structure in a lid plate just above each microwell.

Referring now to FIG. 4, a cross-sectional view of an embodiment of a sample holder 14 of the system 10 is shown. The sample holder may be a microplate assembly 14 as shown in FIG. 4, and may be used with the system 10 described and shown in FIGS. 1A, 1B, and 2, or it may be used with traditional plate reader devices. This embodiment may generally include a bottom plate 74 having a plurality of microwells 16 and a top plate 78 having a plurality of domes 78, each dome substantially corresponding to each microwell 16. The microwells 16 may be very small. For example, each microwell 16 may have a diameter of approximately 300-400 μm and a depth of approximately 20-50 μm, and a volume of approximately 0.02 μL or less. Using microwells 16 this small not only may greatly reduce the cost of expensive reagents used in typical platereader-based assays (such as antibodies and RNA probes), but the small microwell 16 size may allow for the measurement of oxygen consumption in small cell samples. This, in turn, may facilitate the study of cellular heterogeneity and make possible studies of tissues in limited supply (for instance, primary tissues removed from animal models and biopsies from patients). However, the microwells may each have a volume range of approximately 1 μL to approximately 0.01 μL. Further, the opening 80 of each microwell 16 may be substantially circumscribed by a slightly raised lip region 82. For example, the lip region 82 may be approximately 5 μm above the surface of the bottom plate 74 and approximately 1 μm to 10 μm in width.

The microplate assembly 14 (both the bottom plate 74 and top plate 76) may be composed of quartz, instead of plastic or glass as is commonly used in the art. Although plastic microplates may be easy to manufacture, they are permeable to oxygen. Oxygen permeability may limit the accuracy and sensitivity of oxygen consumption measurements, especially when the microwells 16 and samples 18 are small. Although it may be possible to correct for small oxygen leaks in a microplate 14, oxygen-permeable walls can also act as an oxygen buffer, making such corrections difficult. Glass and quartz, on the other hand, display very low oxygen permeability. Additionally, quartz has the advantage of exhibiting less delayed phosphorescence than glass. Because the decay of phosphorescence (excited-state Pt-porphyrin molecules, for example) increases with increased oxygen concentrations, the effect of oxygen concentration on phosphorescence becomes more dramatic at longer intervals following the excitation light flash from the one or more light sources 34; however, at long intervals the signal is also weaker. Quartz may optimize measurement sensitivity y providing lower background noise that would otherwise compete with this weak signal.

Each dome 78 of the top plate 76 may further include one or more sensors 22, such as an oxygen sensor (for example, phosphorescent Pt-porphyrin probes). Each dome 78 may be approximately 200 μm in diameter, and approximately 5 μm deep in order to accommodate the sensor. For example, a phosphorescent Pt-porphyrin probe may be embedded in a dome 78 within a thin film of an oxygen-permeable, hard, hydrophobic silicone resin (such as VacSeal from SPI Supplies, Inc.). Silicone resins may increase the oxygen sensitivity of Pt-porphyrin, and hard silicone resins may also help prevent Pt-porphyrin from leaching out. Putting an oxygen sensor 22 in contact with a sample 18 may produce inaccurate measurements because of oxygen gradients that may exist near the sample 18 cells. Placement of a sensor 22 in a dome 78 above a sample 18, on the other hand, may allow for a more accurate measurement of the average oxygen consumption within the sample 18. The bottom of each microwell 16 may be optionally coated with a layer of poly-L-lysine or Cell Tak (from BD Biosciences) to adhere sample cells 18 to the microwells 16.

Figure 5:
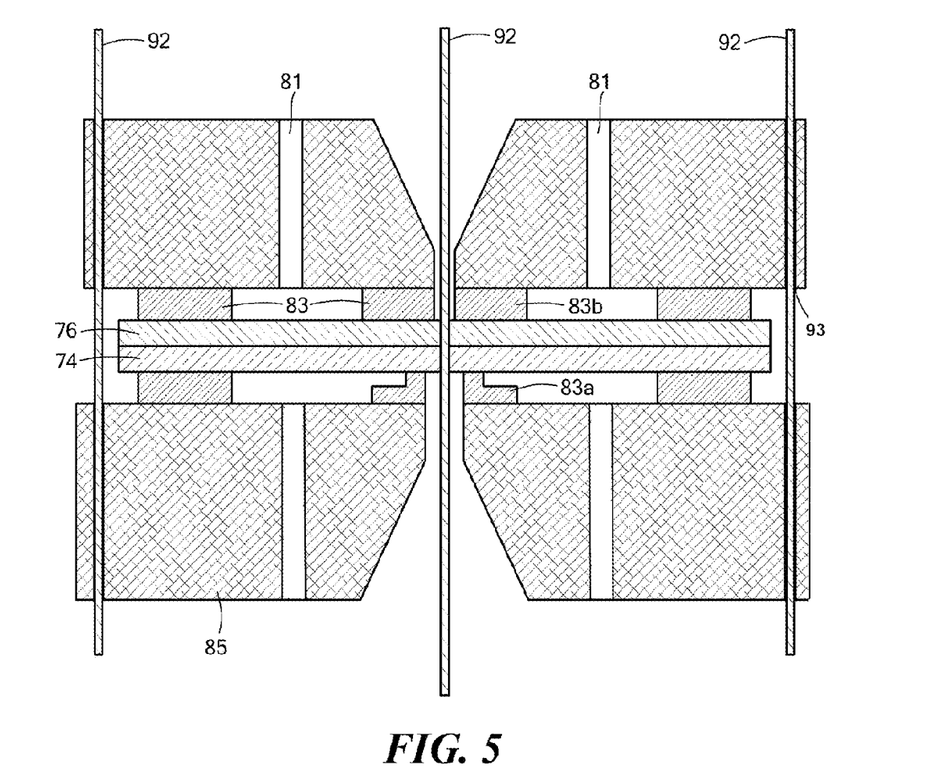
FIG. 5 shows a cross-section view of an embodiment of an assembly for etching the lid plate and bottom plate of the microplate apparatus.

Referring now to FIG. 5, a method of creating the microplate assembly 14 is shown. To create the microplate assembly 14 as described and shown in FIG. 4, a plurality of microwells 16 may be etched into a first quartz plate, thereby forming the bottom plate 74 of the microplate 14. Alternatively, a plurality of microwells 16 may be etched into a glass plate, such as a microscope slide. Likewise, a matching plurality of domes 78 may likewise be etched into a second quartz (or glass) plate, thereby forming the top plate 76. The microwells 16 and domes 78 may be etched using precisely aligned Teflon® or polypropylene masks 83 that are clamped onto the quartz or glass plates using high pressure. For example, as shown in FIG. 5, a first mask 83a (made of Teflon, polypropylene, or other pliable material resistant to the etching solution used, such as hydrofluoric acid and hexafluoric acid) may be affixed (for example, using an epoxy adhesive) to a solid element, such as a Lucite block 85, and then placed in contact with the bottom plate 74. An etching solution, such as 6% hydrofluoric acid and 5% hexafloric acid, may be injected through one or more etching solution injection holes 81 to contact the plates 74, 76. The first mask 83a may be configured to allow an etching solution (such as hydrofluoric acid or a mixture of 6% hydrofluoric acid and 5% hexafloric acid) to create the plurality of microwells 16 each having a lip region 82 that may circumscribe the opening 80 of the microwell 16. Alternatively, the lip regions 82 may be created by removing the mask 83 from the bottom plate 74 and etching solution applied to the areas surrounding the microwells 16 except for the areas substantially circumscribing each microwell 16, which will become the lip regions 82. A second mask 83b may be likewise affixed to a block 85, and then placed in contact with the top plate 76 to create the plurality of domes 78. Lucite blocks may be held in place relative to the plates 74, 76 and blocks 85 using one or more alignment pins 92 that fit into one or more alignment holes 94 in the masks 83a, 83b and/or blocks 85. After the etching solution has been in contact with the plates 74, 76 for an appropriate period of time, water or other solution may be injected through the etching solution injection holes 81 to wash away excess etching solution and stop the etching process. Continuous agitation by a vertical vibrator may speed up removal of dissolved quartz or glass components near the plate surface, and may greatly enhance both the rate and uniformity of etching. Once the silicone resin containing the Pt-porphyrin sensor 22 is applied to the domes 78, the top plate 76 may be cured at approximately 120° C. for approximately two hours, then further cured at room temperature for approximately two weeks.

As a non-limiting example, microwells 16 formed in this manner may be approximately 300-400 μm in diameter, approximately 20-50 μm in depth, and may have a volume of approximately 0.02 μL. Applying the etching solution for a short amount of time, such as approximately 5 minutes, may result in the formation of plateau-like lip regions 82 that substantially circumscribe the opening 80 of each microwell 16 and allow for a an oxygen-tight seal around each microwell 16. When the bottom 74 and top plates 76 are put in contact with each other under pressure, visible "optical fringe" patterns may indicate the formation of a tight seal. When the bottom plate 74 and top plate 76 are in contact with each other, the lip regions 82 may define an outer space 84 external to the microwells 16 between the two plates 74, 76 (that is, an internal space within the bottom 74 and top 76 plates).

Figure 6A:
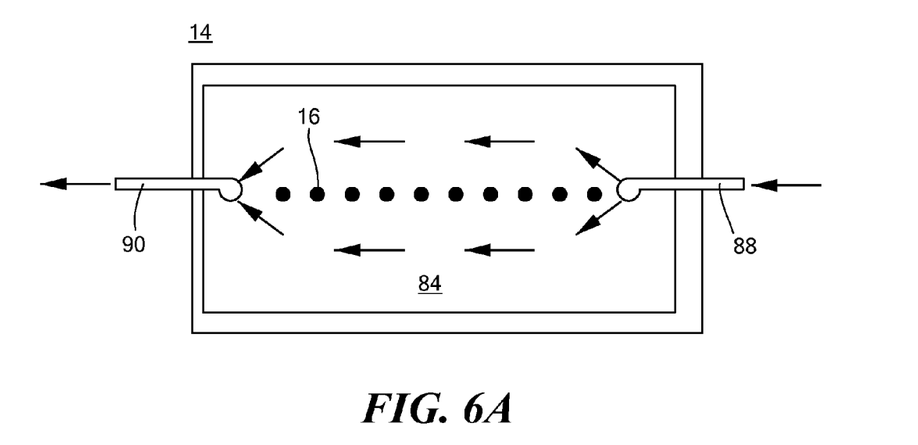
FIGS. 6A, 6B, and 6C show a cross-section view of a microplate apparatus and a means for changing the solution in the microwells.
Figure 6B:
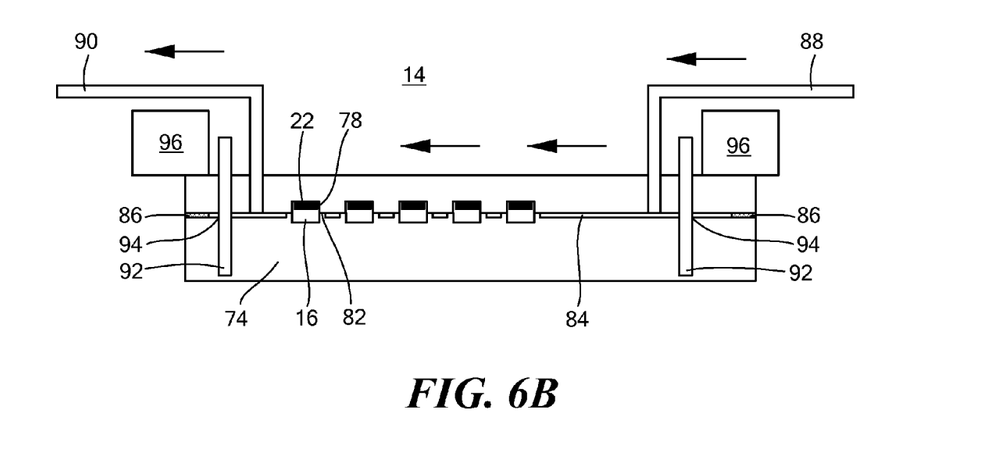
Figure 6C:
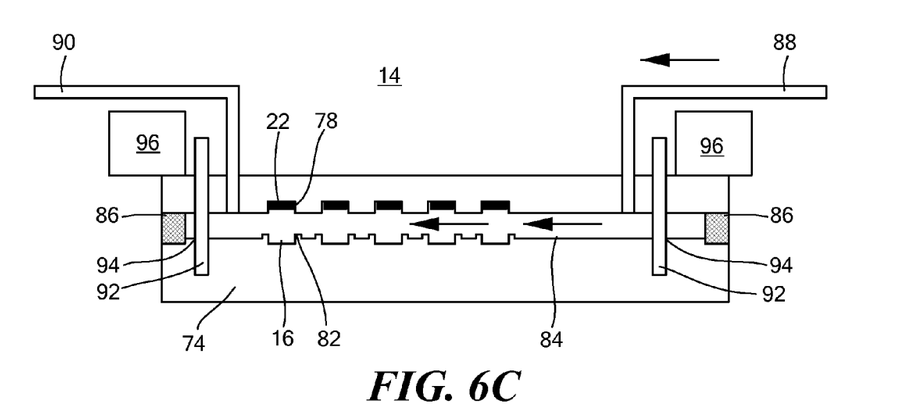

Referring now to FIGS. 6A-6C, a cross section of a microplate 14 apparatus of the system and a means for changing the solution in the microwells 16 is shown. In addition to a bottom plate 74 having a plurality of microwells 16 and a top plate 76 having a plurality of corresponding domes 78, each with a sensor 28, the microplate 14 may further include a compressible gasket 86, an inlet tube 88, and an outlet tube 90 (FIG. 6A, top view) to facilitate sealing the bottom 74 and top plates 76 and for unsealing the two plates and changing solution contained within the microwells 16. For example, this system may allow for the sequential addition of various substrates and drugs that are important for measuring the function of various components of the mitochondrial electron transport chain, without damaging or washing out the sample cells 18. Additionally, this system may prevent the entry of atmospheric oxygen into the microwells 16 when the solutions are changed or reagents added. Arrows indicate the direction of flow of solutions, substrates, drugs, reagents, or any additional fluids injected through the inlet tube 88.

Figure 7A:
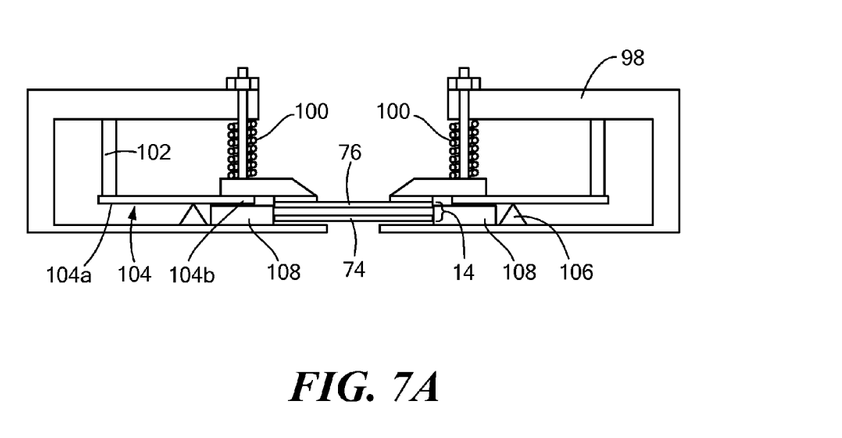
FIGS. 7A and 7B show a cross-section view and an elevation view of a clamping apparatus for changing the solution in the microwells of the microplate apparatus.
Figure 7B:
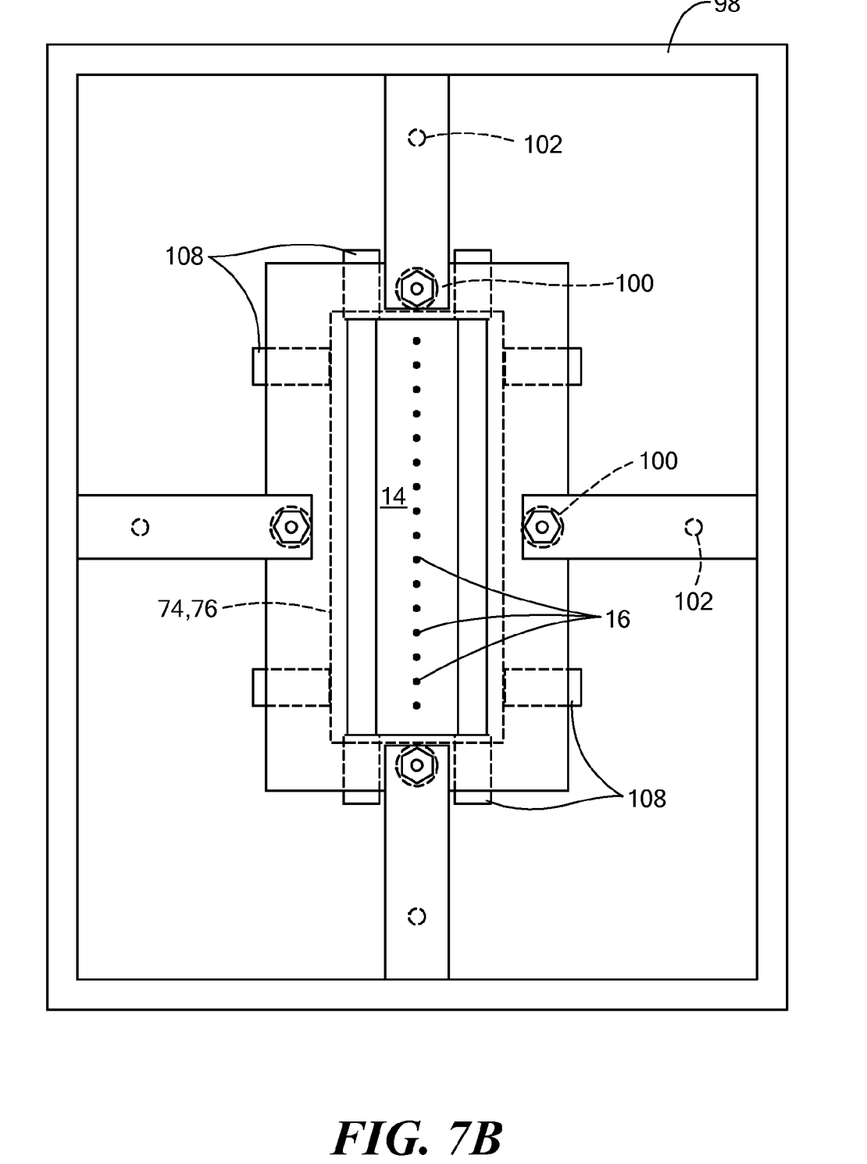

Referring now to FIG. 6B (side view), the bottom plate 74 and the top plate 76 may be aligned using one or more alignment pins that are releasably engageable with matching holes 94 in the bottom 74 and top 76 plates. During use, the bottom 74 and top 76 plates may be clamped together or sealed together using vacuum pressure. A clamping system 91 suitable for sealing the microplate apparatus 14 is shown in greater detail in FIG. 7, and may include a compression spring system using solenoids to release the pressure on the bottom 74 and top 76 plates.

The compressible gasket 86, which may be composed of silicone, may be located between the two plates 74, 76, circumscribing the outer edge of the microplate 14. The gasket 86 may be compressed when the two plates 74, 76 are sealed, and may be of any thickness that allows for the separation of the two plates 74, 76 at a distance of, for example, approximately 500 μm. When the gasket 86 is compressed, the two plates 74, 76 may be in contact with each other via the lip regions 82 substantially circumscribing the opening 80 of each microwell 16, which form a tight seal between each microwell 16 and its corresponding dome 78. This tight seal may prevent oxygen from diffusing into our out of the microwells 16.

Continuing to refer to FIG. 6B, each microwell 16 may contain a sample 18, which may be a cell suspension, slurry, or other fluid. While the two plates 74, 76 are sealed together, a new solution may be injected through the inlet tube 88, may flow into the out space 84 between the two plates 74, 76 (that is, space outside the individual microwells 16), then may exit the microplate apparatus 14 through the outlet tube 90. The clamping or vacuum pressure keeping the plates 74, 76 together may be released and the outlet tube 90 closed, at which point the fluid pressure from the solution within the outer space 84 may lift the top plate 76 until it reaches a stop element 96. The stop element 96 may, for example, allow a separation between the bottom 74 and top 76 plates of approximately 500 μm, which may be sufficient to enable complete equilibration between the old and new solutions within the small microwells 16. After the new solution is added, the outlet valve 90 may be re-opened, the two plates 74, 76 slowly pressed together (such as by the clamping system 91 of FIG. 7), ejecting excess new solution through the outlet tube 90 and resealing the microwell 16/dome 78 compartments.

Referring now to FIG. 6C (side view), separation of the two plates 75, 76 is shown. To separate the plates 74, 76, fluid pressure (such as from the clamping system 91) may be applied through an inlet tube in the lid plate to force the plates apart and allow new solution to enter the microwells 16. The fluid pressure may be provided by the pressurized flow of the fresh solution when stale solution is changed. The microplate assembly 14 may include a trough, in fluid communication with the input tube, between the two plates that acts as a conduit of the solution to the space between the plates 74, 76 and so ultimately to the microwells 16.

Referring now to FIG. 7, a clamping system 91 is shown. The clamping system may generally include a frame 98 that is at least partially in contact with the plates 74, 76. The frame 98 may include an inner frame portion 98a at least partially in contact with the top plate 76 and an outer frame portion 98b at least partially in contact with the bottom plate 74. Affixed between the inner frame portion 98a and outer frame portion 98b may be one or more compression springs 100 that each exert a downward pressure on the inner frame portion 98a, which, in turn, may exert a downward pressure on the microplate assembly 14, pressing together the bottom 74 and top plates 76. Affixed to the outer frame portion 98b may be one or more solenoids 102 that each exert a downward pressure on one or more release levers 104. Each release lever 104 may be in contact with a fulcrum 106 and have a first end 104a that may be in contact with a solenoid 102, and a second end 104b that may be in contact with the inner frame portion 98a. For example, the clamping assembly 91 may include four compression springs 100, solenoids 102, release levers 104, one on each side of the clamping assembly 91 (as shown in FIG. 7). The frame 98 of the clamping system 91 may also include an aperture 105 that allows light to pass into and out of the microwells 16 when the clamping system 91 is affixed to the microplate assembly 14. Further, the frame 98 may include one or more guides 108 to stabilize the plates 74, 76 during the solution-change process.

When downward pressure is exerted by the solenoids 102 on the first ends 104a of the release levers 104 (such as by applying an electrical current through the solenoids 102), the downward pressure exerted by the compression springs 100 on the inner frame portion 98a may be overcome by the solenoids 102 and the release levers 104 may each pivot on a fulcrum 106 and, in turn, exert upward pressure on the inner frame portion 98a. When upward pressure is exerted on the inner frame portion 98a, the inner frame portion 98a may be lifted away from the microplate assembly 14. Solution may be allowed to then flow through the inlet tube 88 into the microplate assembly 14, lifting the top plate 76 until it reaches the stop element 96. The plates 74, 76 may be clamped together and excess solution expelled through the outlet tube 90 when the downward pressure from the solenoids 102 is released (such as by discontinuing the electric current applied to the solenoid 102). The downward pressure exerted by the compression springs 100 on the inner frame portion 98a may clamp together the plates 74, 76.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A microplate apparatus comprising:
   a lid plate having a thickness and a plurality of indentations, each indentation having a depth that is less than the thickness of the lid plate, each indentation including a film of oxygen-permeable silicone covering at least a portion of each indentation;
   a bottom plate having a plurality of microwells, each one of the plurality of microwells in registration with one of the plurality of indentations;
   one or more sensors embedded within the film of oxygen-permeable silicone in each indentation;
   a compressible gasket disposed between and in contact with an outer edge of the lid plate and an outer edge of the bottom plate, thereby providing a seal between the lid plate and bottom plate, the compressible gasket, lid plate, and bottom plate defining an internal space when the lid plate and bottom plate are spaced apart but in contact with the compressible gasket; and
   an inlet tube and an outlet tube each being in fluid communication with the internal space.

2. The microplate apparatus of claim 1, the bottom plate further including a plurality of lip regions, each of which protruding from the bottom plate and each of which substantially circumscribing each microwell.

3. The microplate apparatus of claim 2, wherein the lid plate and bottom plate are composed of quartz or glass.

4. The microplate apparatus of claim 3, wherein when the lip regions of the bottom plate are in contact with the lid plate, the contact between the lip regions of the bottom plate and the lid plate causing the formation of a substantially gas-tight seal between the plurality of indentations of the lid plate and the plurality of microwells of the bottom plate.

5. The microplate apparatus of claim 4, further including a stop element, the lid plate being lifted above the bottom plate by a fluid when the fluid is injected through the inlet tube into the internal space, the stop element being located at a position above the lid plate such that the stop element allows the lid plate to rise to a maximum height that creates a distance of no more than 500 microns between the lid plate and the bottom plate.

6. The microplate apparatus of claim 5, wherein the one or more sensors include at least one of: pH sensor, oxygen sensor, fluorescent/phorphorescent probe, phosphorescent fluorescent temperature sensor, nitric oxide sensor, and standard fluorescent probe.

7. The microplate apparatus of claim 6, wherein the one or more sensors are Pt-porphyrin probes.

8. The microplate apparatus of claim 6, the microplate apparatus further including a material capable of adhering biological cells, wherein the material capable of adhering biological cells coats at least a portion of the bottom of each of the plurality of microwells.

9. The microplate apparatus of claim 6, wherein each microwell has a volume of approximately 0.001 µL to approximately 0.2 µL.

\* \* \* \* \*